(12) United States Patent
Schlinz et al.

(10) Patent No.: US 6,679,869 B1
(45) Date of Patent: Jan. 20, 2004

(54) ABSORBENT ARTICLE HAVING AN ELASTIC OUTER COVER

(75) Inventors: Daniel Robert Schlinz, Greenville, WI (US); Duane Girard Uitenbroek, Little Chute, WI (US); Thomas W. Odorzynski, Green Bay, WI (US); Jody D. Suprise, Pine River, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 18 days.

(21) Appl. No.: 09/640,165

(22) Filed: Aug. 16, 2000

(51) Int. Cl.$^7$ ................................................ A61F 13/15
(52) U.S. Cl. ........................ 604/385.22; 604/385.02; 604/385.27
(58) Field of Search .............................. 604/358, 362, 604/367, 375, 385.01, 385.23, 387, 385.22, 385.24, 385.27

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,341,216 A | 7/1982 | Obenour ................... 128/287 |
| 4,663,220 A | 5/1987 | Wisneski et al. |
| 4,681,578 A | 7/1987 | Anderson et al. |
| 4,704,116 A | 11/1987 | Enloe |
| 4,726,976 A | 2/1988 | Karami et al. |
| 4,834,738 A | 5/1989 | Kielpikowski et al. |
| 4,842,596 A | 6/1989 | Kielpikowski et al. |
| 4,872,871 A | 10/1989 | Proxmire et al. |
| 4,883,707 A | 11/1989 | Newkirk |
| 4,940,464 A | 7/1990 | Van Gompei et al. |
| 4,965,122 A | 10/1990 | Morman |
| 5,046,272 A | 9/1991 | Vogt et al. |
| 5,104,116 A | 4/1992 | Pohjola |
| 5,135,521 A | 8/1992 | Luceri et al. |
| 5,143,679 A | 9/1992 | Weber et al. |
| 5,151,092 A | 9/1992 | Buell et al. |
| 5,167,897 A | 12/1992 | Weber et al. |
| 5,196,000 A | 3/1993 | Clear et al. |
| 5,224,405 A | 7/1993 | Pohjola |
| 5,226,992 A | 7/1993 | Morman |
| 5,591,151 A | 1/1997 | Hasse et al. ............. 604/385.1 |
| 5,820,617 A | 10/1998 | Igaue et al. |
| 5,938,648 A * | 8/1999 | LaVon et al. ............. 604/358 |
| 5,997,989 A | 12/1999 | Gessner et al. |
| 6,001,751 A | 12/1999 | Pereira et al. |
| 6,015,936 A | 1/2000 | Takai et al. |
| 6,177,607 B1 * | 1/2001 | Blaney et al. ............. 604/378 |
| 6,231,555 B1 * | 5/2001 | Lynard et al. .......... 604/385.01 |

FOREIGN PATENT DOCUMENTS

| | | | |
|---|---|---|---|
| EP | 0 217 032 | 4/1987 | ......... D04H/13/00 |
| EP | 0 412 549 A1 | 8/1990 | ......... A61F/13/15 |
| EP | 0 71-472 A1 * | 5/1996 | ......... A61F/13/15 |
| EP | 0 714 647 A3 | 6/1996 | ......... A61F/13/15 |
| EP | 0 714 647 A2 | 6/1996 | ......... A61F/13/15 |
| EP | 832 629 A2 | 4/1998 | ......... A61F/13/15 |
| EP | 0 832 629 A3 | 4/1998 | ......... A61F/13/15 |
| EP | 0 967 953 B1 | 9/2002 | |
| WO | WO 95/18589 | 7/1995 | ......... A61F/13/15 |
| WO | WO 00/30584 | 6/2000 | ......... A61F/13/15 |

* cited by examiner

*Primary Examiner*—Weilun Lo
*Assistant Examiner*—Jacqueline F Stephens
(74) *Attorney, Agent, or Firm*—Pauley Petersen & Erickson

(57) ABSTRACT

A laminate including an elastic nonwoven layer and a barrier film layer can stretch freely and provide a high level of breathability. The elastic layer and the film layer can be minimally bonded to one another, such as around a periphery of one or both layers. The laminate is particularly suitable for making absorbent articles.

32 Claims, 5 Drawing Sheets

ABSORBENT ARTICLE HAVING AN ELASTIC OUTER COVER

FIELD OF THE INVENTION

This invention is directed to a laminate having independently movable elastic and film layers. The laminate is particularly suitable for use as an outer cover for absorbent articles.

BACKGROUND OF THE INVENTION

Absorbent articles typically include a film layer to prevent fluids, such as bodily wastes, from leaking through the article. Such films can be breathable, thereby allowing vapors to escape while maintaining the liquids within the article. Absorbent articles typically also include elastic elements in order to create a form-fit in such areas as leg openings and waist openings.

Two or more types of material can be layered together to create a laminate that includes the properties of each material therein. For example, the process of "zero strain" stretch bonding, as disclosed in U.S. Pat. Nos. 5,143,679 and 5,167,897 both issued to Weber, et al., includes bonding at least two layers to one another while in an untensioned (hence zero strain) condition. Of the at least two layers, one of the layers is stretchable and elastomeric and another layer is stretchable but not necessarily elastomeric. The laminate is stretched incrementally through the use of one or more pairs of meshing corrugated rolls which reduce the strain rate experienced by the web. The layer that is stretchable but not necessarily elastomeric, upon being stretched in the laminate, becomes permanently elongated, at least to a degree, so that the laminate will not return to its original undistorted condition upon release of the stretching force. The resulting laminate has z-direction bulking and elastic extensibility in the direction of initial stretching at least up to the point of initial stretching.

Absorbent articles made with a zero strain stretch laminate composite elastic material, such as the absorbent articles disclosed in U.S. Pat. No. 5,151,092 issued to Buell, et al., and U.S. Pat. No. 5,196,000 issued to Clear, et al., have discrete elasticized portions, such as side panels and waist bands. An inherent property in the zero strain stretch laminate is the z-direction bulking which is therefore present in the absorbent articles made with such material. Furthermore, the elastic extensibility of the zero strain stretch laminate is limited to the point of initial stretching. Human beings, particularly babies, are typically active and vary greatly in terms of body contours. Absorbent garments worn by such active people must be able to move with the wearer and remain close to the wearer's skin to avoid leakage from the garment.

Necked spunbond and solid stretch film laminates have been proposed as outer covers that provide superior fit. These designs must stretch, breathe, engage fastener hooks and be aesthetically pleasing all with the same material.

There is a need for a lower priced laminate, suitable for making absorbent articles, that can stretch freely and also provide a high level of breathability.

There is a further need for a laminate, suitable for making absorbent articles, that can provide an aesthetically pleasing appearance at a relatively low cost without fear of leakage.

SUMMARY OF THE INVENTION

The present invention is directed to a laminate that can stretch freely and provide a high level of breathability. This laminate is particularly suitable for making absorbent articles. Furthermore, this laminate is relatively inexpensive to produce and provides an aesthetically pleasing appearance when used to make absorbent articles.

The laminate includes an elastic nonwoven layer, and a barrier film at least partially bonded to the elastic nonwoven layer. The barrier film and the elastic nonwoven layer can suitably be bonded just about the periphery of one or both layers.

The barrier film can have a wide range of breathability, including a WVTR of over 5000 grams/m$^2$-24 hours. The elastic nonwoven layer can be any fiberous, or cloth-like, breathable elastic layer. For example, the elastic nonwoven layer can include a neck-bonded laminate, a stretch-bonded laminate, a spunbond-meltblown-spunbond laminate, a spunbonded laminate, or a meltblown laminate.

An absorbent article can be made from the laminate of the invention. For example, the laminate can be used as an outer cover, or backsheet, of a diaper or training pant. The barrier layer and the elastic nonwoven layer can be bonded together just around the leg openings and the waist opening, thereby providing great flexibility so that the elastic layer can move independently of the film layer. In addition, an elastic waistband can be attached to the garment around the waist opening and can be partially elongated when attached, so that the waist opening is maintained closely around the wearer's waist to prevent leakage from the garment. The laminate of the invention can also be used to make swim wear, adult incontinence garments, feminine hygiene products, or medical products.

With the foregoing in mind, it is a feature and advantage of the invention to provide a laminate, suitable for making absorbent articles, that can stretch freely and also provide a high level of breathability.

It is also a feature and advantage of the invention to provide an absorbent article having great flexibility and high breathability.

It is also a feature and advantage of the invention to provide a method of preparing a laminate with independently movable layers.

The foregoing and other features and advantages will become further apparent from the following detailed description of the presently preferred embodiments, read in conjunction with the drawings.

DEFINITIONS

Figure 1:
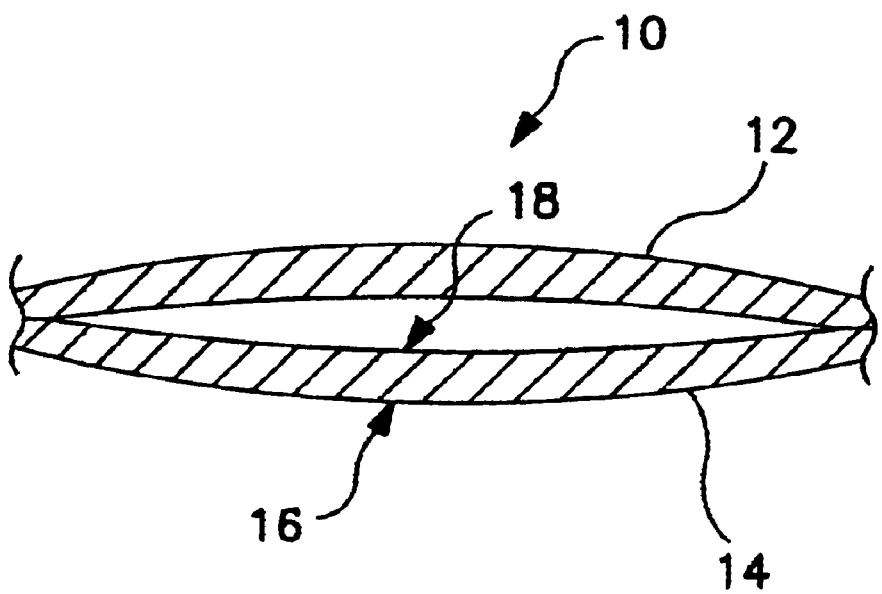
FIG. 1 is a sectional view of one embodiment of the laminate of the invention.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 50 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flexible" refers to materials which are compliant and which will readily conform to the general shape and contours of the wearer's body.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 3:
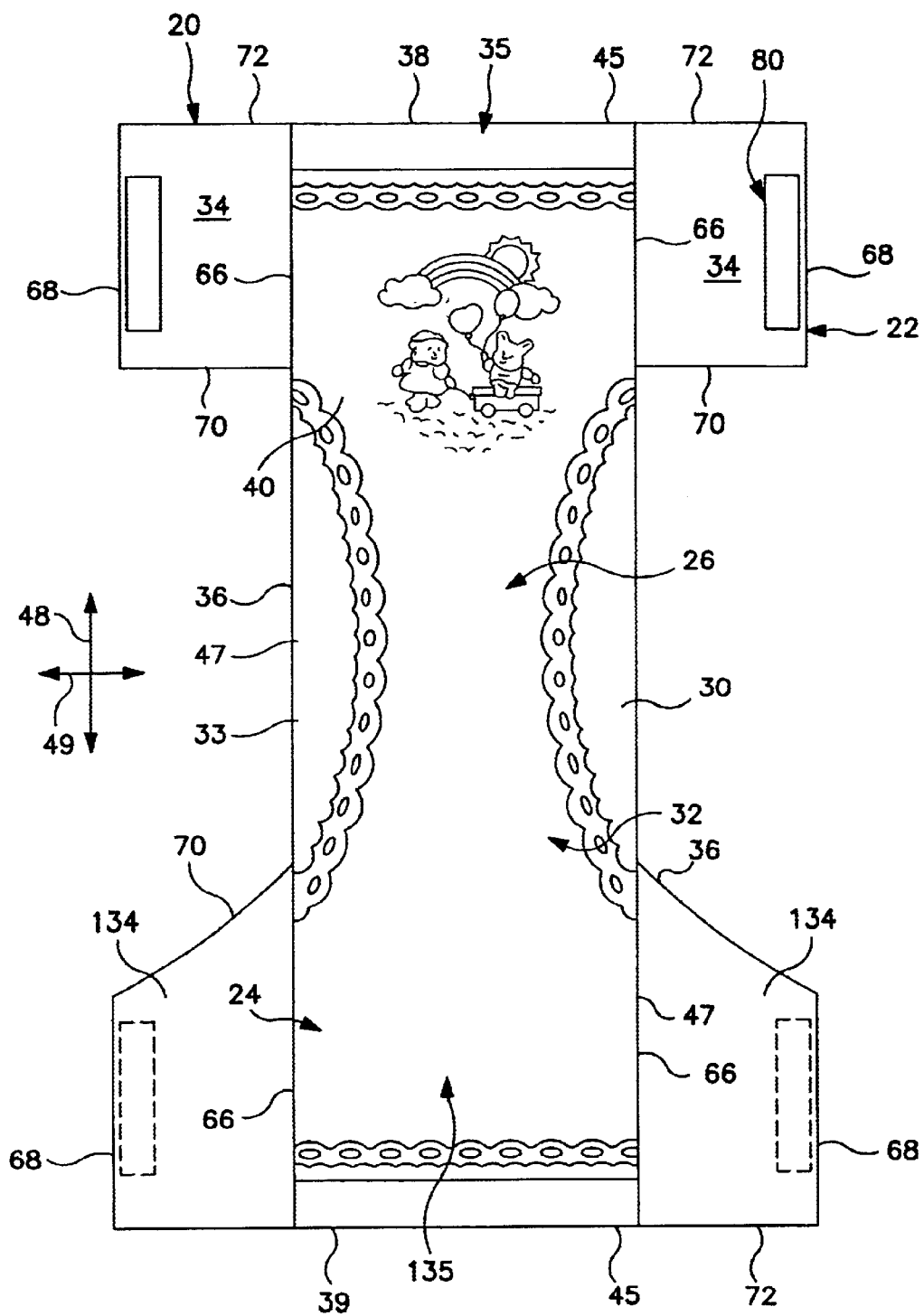
FIG. 3 is a plan view of an absorbent garment in a partially disassembled, stretched flat state, and showing the surface of the article that faces away from the wearer when the article is worn.
Figure 4:
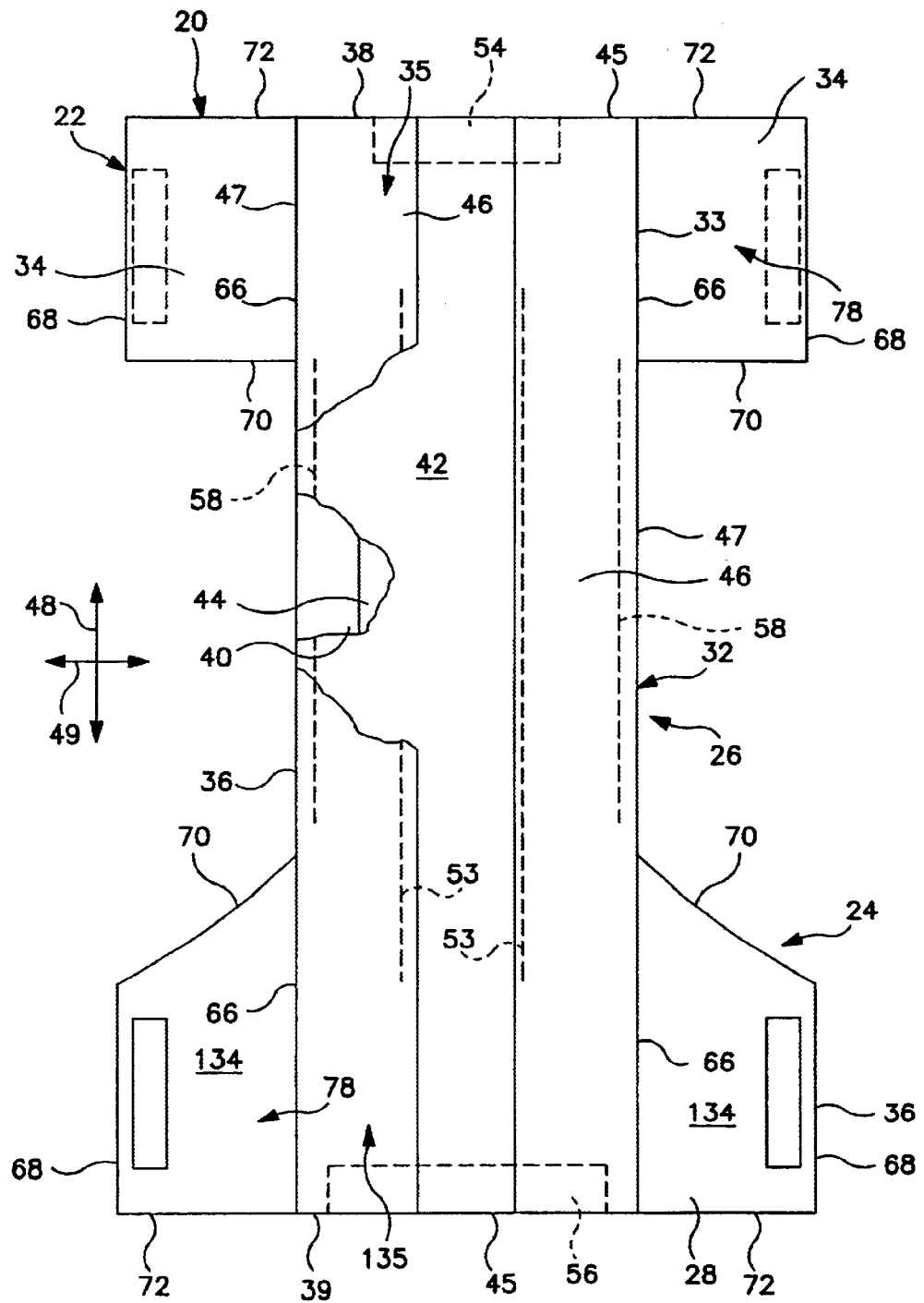
FIG. 4 is a plan view of the absorbent garment of FIG. 3 in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes depicted in FIGS. 3 and 4. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Neck-bonded laminate" refers to a laminate wherein at least one layer of fabric, nonwoven web or sub-laminate is drawn such that it is extended under conditions reducing its width or its transverse dimension by stretching lengthwise or increasing the length of the fabric. The controlled drawing may take place under cool temperatures, room temperature or greater temperatures and is limited to an increase in overall dimension in the direction being drawn up to the elongation required to break the fabric, nonwoven web or laminate, which in most cases is about 1.2 to 1.6 times. When relaxed, the fabric, nonwoven web or sub-laminate does not return totally to its original dimensions. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 issued to Morman, and commonly assigned to the assignee of the present invention, discloses a reversibly necked nonwoven material which may be formed by necking the material, then heating the necked material, followed by cooling and is incorporated herein by reference in its entirety. The heating of the necked material causes additional crystallization of the polymer giving it a partial heat set. If the necked material is a spunbond web, some of the fibers in the web may become crimped during the necking process, as explained in U.S. Pat. No. 4,965,122.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a nonelastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

Referring to FIG. 1, a laminate 10 is shown including an elastic nonwoven web layer 12 and a barrier film layer 14. Due to separation between the elastic layer 12 and the film layer 14, the laminate 10 can freely stretch and can maintain a wide range of breathability. The elastic layer 12 has a cloth-like texture and can include a neck-bonded laminate or a stretch-bonded laminate. Methods of making such materials are well known to those skilled in the art and described in U.S. Pat. No. 5,226,992 issued Jul. 13, 1993 to Morman; and European Patent Application No. EP 0 217 032 published on Apr. 8, 1987 in the names of Taylor et al.; both of which are incorporated herein by reference. Other suitable elastic nonwoven materials include a spunbond-meltblown-spunbond laminate, another spunbonded laminate, or another meltblown laminate.

Other materials suitable for use in preparing the elastic nonwoven web 12 include diblock, triblock, or multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E.I. Du Pont de Nemours Co., under the trade name HYTREL® polyester; and single-site or metallocene-catalzed polyolefins having density less than about 0.89 grams/cc, available from Dow Chemical Co. under the trade name AFFINITY®. Other suitable elastomeric polymers may also be used to make the elastic nonwoven web 12. These include, without limitation, elastomeric (single-site or metallocene catalyzed) polypropylene, polyethylene and other alpha-olefin homopolymers and copolymers, having density less than about 0.89 grams/cc; ethylene vinyl acetate copolymers; and substantially amorphous copolymers and terpolymers of ethylene-propylene, butene-propylene, and ethylene-propylene-butene.

The film layer 14 is microporous and has minimal stretch. Breathability of the film layer 14 can vary greatly, and is suitably at least 500 grams/$M^2$-24 hours, more suitably at least 1000 grams/$m^2$-24 hours, desirably at least 5000 grams/$m^2$-24 hours, determined from the WVTR test procedure described below. The microporous quality of the film layer 14 readily permits molecular diffusion of moisture vapor between a first surface 16 of the film layer 14 and a second surface 18 of the film layer 14. Suitable materials for the film layer 14 include polyolefin films and any other suitable polymeric films that are liquid impermeable and vapor permeable.

One particular material suitable for the film layer 14 is a self-regulating film that includes a polymer matrix component and a water-swellable filler component. The polymer matrix preferably includes a polyolefin, and constitutes about 30–90% by weight of the film layer. The self-regulating film layer 14 also includes a filler component that can be water-swellable and/or non-water-swellable. The filler component may be an organic or inorganic filler, and constitutes about 10–70% by weight of the film layer 14. The filler(s) and polymer matrix component are initially melt blended, and the blend is extruded into a precursor film layer. The precursor film layer may be extruded as a single-layer film, or may constitute one or more layers in a multilayer film structure. The film is then stretched at an elevated temperature below the melting temperature of the polymer component. As the film is stretched, voids form around the filler particles to form a microporous, breathable self-regulating film layer 14.

The self-regulating film layer 14 functions as a typical microporous breathable film during times of low to moderate moisture exposure. The voided film is characterized by thin polymer membranes surrounding the filler particles, and/or fine pore networks, either of which creates a tortuous path so that the film allows the molecular diffusion of water vapor through the film, but does not allow penetration by liquid water. When the vapor penetration becomes excessive, such as when one side of the film is exposed to a saturated or otherwise high vapor concentration or an aqueous liquid, the water-swellable filler particles become wet from condensation and begin to swell, filling the voids to various degrees. By this mechanism, the vapor permeable tortuous paths are reduced or closed off.

The film layer 14 and the elastic layer 12 are partially, but not fully, bonded to one another. For example, if the film layer 14 and the elastic layer 12 have the same length and the same width and are aligned with one another, the two layers can be bonded together about a periphery of each of the layers. If, however, one layer is smaller than the other, the two layers can be bonded together about a periphery of the smaller layer, or about a periphery of a union of the two layers. Alternatively, the two layers can be bonded together in a pattern that allows each layer enough freedom to stretch or move on its own without causing the other layer to move.

Minimal bonding is used to bond the film layer 14 to the elastic layer 12. At least 70% of the bonding is in a peripheral region of at least one of the layers 12, 14. The term "peripheral region" as used herein refers to a region along the periphery of a layer suitably within about 1.5 inches (3.8 cm) of an edge of the layer, desirably within about 0.5 inch (1.3 cm) of an edge of the layer. Desirably, at least 80% of the bonding is in the peripheral region of at least one of the layers 12, 14. More desirably, at least 90% of the bonding is in the peripheral region of at least one of the layers 12, 14. Even 100% of the bonding can suitably be in the peripheral region of at least one of the layers 12, 14. The minimal bonding allows the elastic layer 12 and the film layer 14 to move independently to conform to a wearer's needs, thereby providing great flexibility to improve fit, thus reducing the possibility of leakage. Furthermore, because of the large unbonded region between the film layer 14 and the elastic layer 12, breathability of the film layer 14 is not restricted by the elastic layer 12.

The film layer 14 and the elastic layer 12 can be bonded to one another either adhesively or sonically. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. Examples of suitable adhesives include elastomeric adhesives (i.e. materials capable of at least 75% elongation without rupture), such as aqueous-based styrene butadiene adhesives, neoprene, polyvinyl chloride, vinyl copolymers, polyamides, and ethylene vinyl terpolymers.

The laminate 10 of the invention is particularly suitable for use as an outer cover for any suitable disposable absorbent article. Examples of such suitable articles include diapers, training pants, swim wear, adult incontinence garments, feminine hygiene products, other personal care or health care garments, or the like. The use of the laminate 10 as an outer cover for any of these products improves the fit of the product by providing elastic conformability to the entire outer cover, and also improves air circulation through the product through the use of a highly breathable film layer 14.

Figure 2:
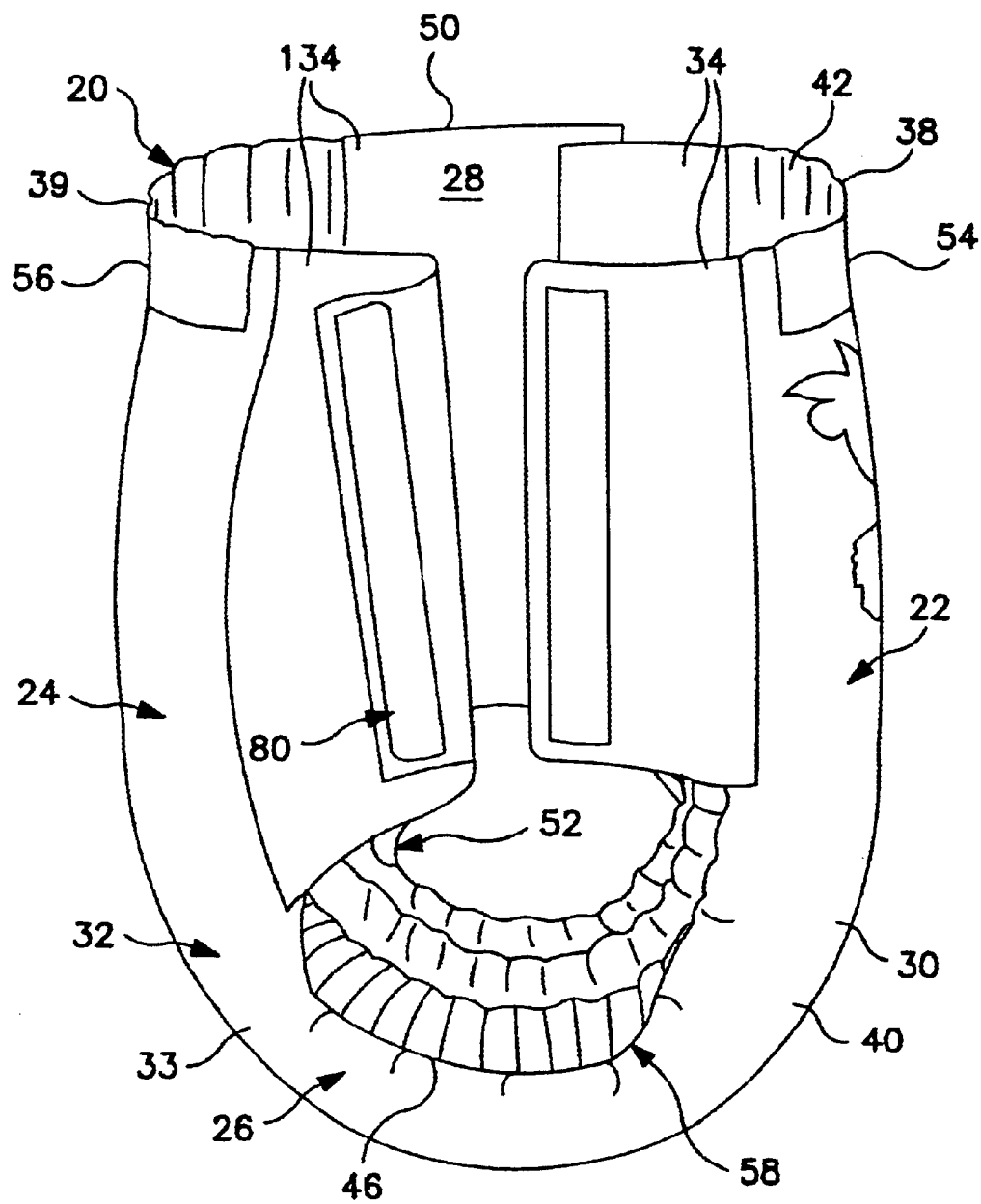
FIG. 2 is a side perspective view of an absorbent garment having an elastic nonwoven outer cover.

Referring to FIG. 2, a disposable absorbent article, such as a training pant 20, is illustrated in a partially fastened condition. The training pant 20 includes an absorbent chassis 32, which includes the laminate 10 as an outer cover 40.

The absorbent chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. With additional reference to FIGS. 3 and 4, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

The illustrated absorbent chassis 32 includes a generally rectangular composite structure 33, a pair of transversely opposed front side panels 34, and a pair of transversely opposed back side panels 134. The composite structure 33 and side panels 34 and 134 may be integrally formed or may include two or more separate elements, as shown in FIGS. 2–4. The illustrated composite structure 33 includes an outer cover 40, a bodyside liner 42 which is connected to the outer cover in a superposed relation, an absorbent assembly 44 (FIG. 4) which is located between the outer cover 40 and the bodyside liner 42, and a pair of containment flaps 46 (FIG. 4). The generally rectangular composite structure 33 has opposite linear end edges 45 that form portions of the front and back waist edges 38 and 39, and opposite linear side edges 47 that form portions of the side edges 36 of the absorbent chassis 32 (FIGS. 3 and 4). For reference, arrows 48 and 49 depicting the orientation of the longitudinal axis and the transverse axis, respectively, of the training pant 20 are illustrated in FIGS. 3 and 4.

With the training pant 20 in the fastened position as partially illustrated in FIG. 2, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The outer cover 40 includes the laminate 10 of the invention. The elastic layer 12 provides a generally cloth-like texture for an outer surface of the outer cover. As mentioned, the elastic layer 12 can include a neck-bonded laminate, a stretch-bonded laminate, a spunbondmeltblown-spunbond laminate, a spunbonded laminate, or a meltblown laminate. One example of such a material is a 20 gsm (grams per square meter) spunbond polypropylene nonwoven web.

The film layer 14 of the laminated outer cover 40 is substantially liquid impermeable, can have any of a wide range of breathability, and has minimal stretchability. The film layer 14 is desirably manufactured from a thin plastic film and prevents waste material from wetting articles, such as bedsheets and clothing, as well as the wearer and care giver. A suitable liquid impermeable film for use as the film layer 14 is a 0.2 millimeter polyethylene film commercially available from Huntsman Packaging of Newport News, Va., U.S.A. The liquid impermeable film layer 14 can permit vapors to escape from the interior of the disposable absorbent article 20, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

As in the laminate 10 alone, the elastic layer 12 and the film layer 14, when used as the outer cover 40, are partially bonded to one another. For example, the elastic layer 12 and the film layer 14 can be bonded to one another around the waist opening 50 and the leg openings 52 of the garment. Additional bonding may be included as well.

The front region 22 of the absorbent chassis 32 includes the transversely opposed front side panels 34 and a front center panel 35 (FIGS. 3 and 4) positioned between and interconnecting the side panels, along with a front waist elastic member 54 and any other connected components. The back region 24 of the absorbent chassis 32 includes the transversely opposed back side panels 134 and a back center panel 135 (FIGS. 3 and 4) positioned between and interconnecting the side panels, as well as a rear waist elastic member 56 and any other connected components. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The transversely opposed front side panels 34 and transversely opposed back side panels 134 can be permanently bonded to the composite structure 33 of the absorbent chassis 32 in the respective front and back regions 22 and 24, and are releasably attached to one another by a fastening system 80. More particularly, as shown best in FIGS. 3 and 4, the front side panels 34 can be permanently bonded to and extend transversely beyond the linear side edges 47 of the composite structure 33 in the front region 22 along attachment lines 66, and the back side panels 134 can be permanently bonded to and extend transversely beyond the linear side edges of the composite structure in the back region 24 along attachment lines 66. The side panels 34 and 134 may be attached using attachment means known to those skilled in the art such as adhesive, thermal or ultrasonic bonding. The side panels 34 and 134 can also be formed as extensions of the outer cover 40.

The absorbent chassis 32 is configured to contain and/or absorb any body exudates discharged from the wearer. For example, the absorbent chassis 32 desirably although not necessarily includes the pair of containment flaps 46 which are configured to provide a barrier to the transverse flow of body exudates. A flap elastic member 53 (FIG. 4) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes the front waist elastic member 54, the rear waist elastic member 56, and leg elastic members 58, as are known to those skilled in the art (FIG. 4). The waist elastic members 54 and 56 can be operatively joined to the outer cover 40 and/or bodyside liner 42 along the opposite waist edges 38 and 39, and can extend over part or all of the waist edges. The waist elastic members 54 and 56 can be relaxed or partially elongated when joined to the outer cover 40 and/or bodyside liner 42, thereby resulting in a high performance effect.

The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A. In another particular embodiment, the waist elastic members 54 and 56 can be partially elongated when attached to the chassis 32, such that the waist elastic members 54 and 56 provide a seal around a wearer's waist, yet can also expand along with the elastic layer 12 when the wearer moves.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the wearer's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner 42 can be composed of a meltblown or spunbonded web of polyolefin fibers. The bodyside liner 42 can also be a bonded-carded web composed of natural and/or synthetic fibers. The bodyside liner 42 can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Hodgson Textile Chemicals of Mount Holly, N.C., U.S.A. and GLUCOPON® 220UP from Henkel Corporation of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 4) is positioned between the outer cover 40 and the bodyside liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article 20, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to a distal edge 68 of the back panel 134, as is best shown in FIGS. 3 and 4.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which is folded over upon itself along an intermediate fold line (not shown).

The side panels 34 and 134 desirably include an elastic material, such as the elastic layer 12, capable of stretching in a direction generally parallel to the transverse axis 49 of the training pant 20. In particular embodiments, the front and back side panels 34 and 134 may each include an interior portion 78 disposed between the distal edge 68 and the respective front or back center panel 35 or 135. In the illustrated embodiment in FIG. 4, the interior portions 78 are disposed between the distal edges 68 and the side edges 47 of the rectangular composite structure 33. The elastic material of the side panels 34 and 134 can be disposed in the interior portions 78 to render the side panels elastomeric in a direction generally parallel to the transverse axis 49. Most desirably, each side panel 34 and 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68 and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate, a neck-bonded laminated, a reversibly necked laminate, or a stretch-bonded laminate material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

Figure 5:
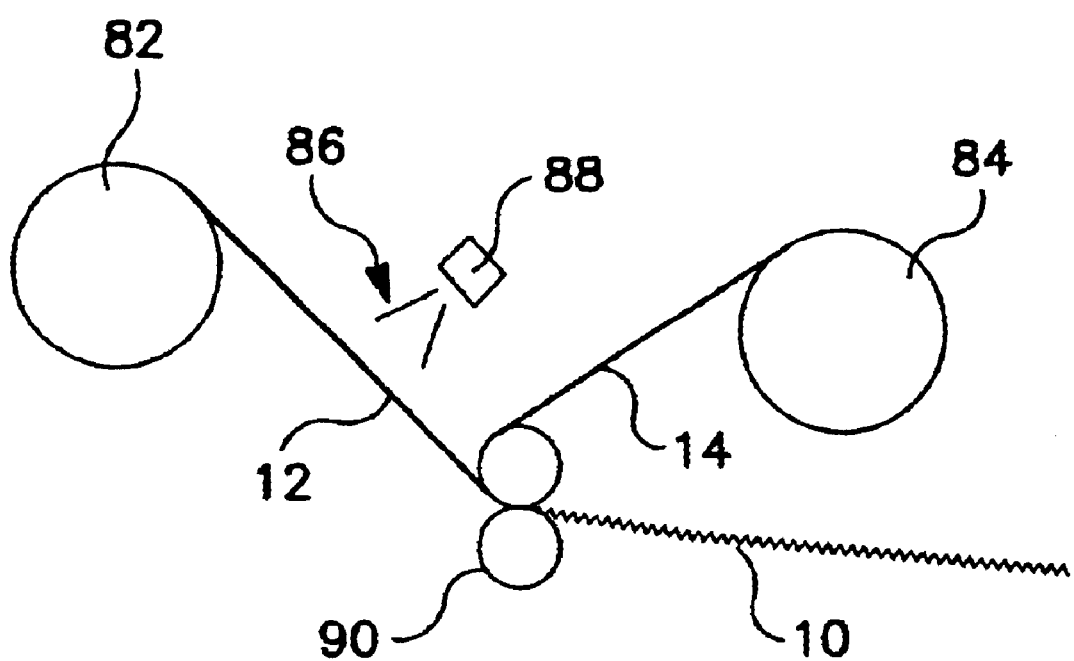
FIG. 5 is a schematic diagram of an integrated process for making a laminate of the invention.

FIG. 5 illustrates a process for forming the laminate 10 of the invention. Prior to the illustrated process, the elastic nonwoven layer 12 is formed and wound onto a roller 82. Also, the film layer 14 is extruded and wound onto a roller 84. As shown in FIG. 5, the elastic layer 12 is unwound from the roller 82 simultaneously while the film layer 14 is unwound from the roller 84. The elastic layer 12 and the film layer 14 are then laminated together. Before the elastic layer 12 and the film layer 14 are laminated, a portion of either the elastic layer 12 or the film layer 14 can be coated or sprayed with an adhesive 86 via an adhesive sprayer 88. The laminate material is then passed through nip rolls 90 (preferably smooth calender rolls) and is relaxed and/or retracted to produce the laminate 10 of the invention. Other means for bonding the laminate material known to those having ordinary skill in the art, such as sonic bonding, may be used in place of the adhesive 86 and the nip rolls 90. Bonding between the elastic layer 12 and the film layer 14 is preferably minimal, in a range of between about 5% and about 60% of a surface area of each layer is bonded, suitably between about 7% and about 50% of the surface area of each layer is bonded, more suitably, between about 10% and about 25% of the surface area of each layer is bonded.

The resulting laminate 10 may be used in a wide variety of personal care absorbent articles and medical articles. Due to the minimal bonding, the elastic layer 12 and the film layer 14 can move independently to conform to a wearer's needs, thereby providing great flexibility to improve fit, thus reducing the possibility of leakage. Furthermore, breathability of the film layer 14 is not restricted by the elastic layer 12. The laminate 10 is relatively inexpensive to produce and provides an aesthetically pleasing appearance in finished products attributable to the elastic layer 12 which conforms to the wearer's body.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

Test Procedure for Water Vapor Transmission Rate (WVTR)

A suitable technique for determining the WVTR (water vapor transmission rate) value of a film or laminate material of the invention is the test procedure standardized by INDA (Association of the Nonwoven Fabrics Industry), number IST-70.4–99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CaIC. The sample material is then sealed in the test cell. Again, water vapor diffuses through the air gap to the guard film and the test material and then mixes with a dry gas flow that sweeps the test material. Also, again, this mixture is carried to the vapor sensor. The computer than calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material, guardfilm, airgap} - TR^{-1}_{guardfilm, airgap}$$

Calculations:

WVTR: The calculation of the WVTR uses the formula:

$$WVTR = F p_{sat}(T) RH / A p_{sat}(T)(1-RH))$$

where:
F=The flow of water vapor in cc/min.,
$p_{sat}(T)$=The density of water in saturated air at temperature T,
RH=The relative humidity at specified locations in the cell,
A=The cross sectional area of the cell, and,
$p_{sat}(T)$=The saturation vapor pressure of water vapor at temperature T.

We claim:

1. A laminate comprising:
an elastic nonwoven layer having a length and a width, and a barrier film having a length and a width substantially equal to the length and the width of the elastic nonwoven layer, the barrier film aligned with and partially bonded to the elastic nonwoven layer, wherein at least 70% of a bonded area is located in a peripheral region of each of the layers, the peripheral region surrounding an unbonded central region.

2. The laminate of claim 1, wherein at least 80% of the bonded area is located in the peripheral region of at least one of the layers.

3. The laminate of claim 1, wherein at least 90% of the bonded area is located in the peripheral region of at least one of the layers.

4. The laminate of claim 1, wherein roughly 100% of the bonded area is located in the peripheral region of at least one of the layers.

5. The laminate of claim 1, wherein the barrier film has a WVTR of at least about 500 grams/m²-24 hours.

6. The laminate of claim 1, wherein the barrier film has a WVTR of at least about 1000 grams/m²-24 hours.

7. The laminate of claim 1, wherein the barrier film has a WVTR of at least about 5000 grams/m²-24 hours.

8. The laminate of claim 1, wherein the elastic nonwoven layer comprises a neck-bonded laminate.

9. The laminate of claim 1, wherein the elastic nonwoven layer comprises a stretch-bonded laminate.

10. The laminate of claim 1, wherein the elastic nonwoven layer comprises a spunbond-meltblown-spunbond laminate.

11. The laminate of claim 1, wherein the elastic nonwoven layer comprises a spunbonded laminate.

12. The laminate of claim 1, wherein the elastic nonwoven layer comprises a meltblown laminate.

13. An absorbent garment comprising:
a chassis having a liquid-permeable bodyside liner, an absorbent core, and a substantially liquid-impermeable outer cover, the chassis defining a pair of leg openings and a waist opening;
wherein the outer cover includes a laminate comprising an elastic nonwoven outer layer having a length and a width, and a barrier film inner layer having a length and a width substantially equal to the length and the width of the outer layer, the inner layer aligned with and partially bonded to the elastic nonwoven outer layer such that at least 70% of a bonded area is located in a peripheral region of each of the layers, the peripheral region surrounding an unbonded central region.

14. The absorbent garment of claim 13, wherein at least 80% of the bonded area is located in the peripheral region of at least one of the layers.

15. The absorbent garment of claim 13, wherein at least 90% of the bonded area is located in the peripheral region of at least one of the layers.

16. The absorbent garment of claim 13, wherein roughly 100% of the bonded area is located in the peripheral region of at least one of the layers.

17. The absorbent garment of claim 13, wherein the barrier film inner layer has a WVTR of at least about 500 grams/m²-24 hours.

18. The absorbent garment of claim 13, wherein the barrier film inner layer has a WVTR of at least about 1000 grams/m²-24 hours.

19. The absorbent garment of claim 13, wherein the barrier film inner layer has a WVTR of at least about 5000 grams/m²-24 hours.

20. The absorbent garment of claim 13, further comprising an elastic waistband attached to the chassis around the waist opening.

21. The absorbent garment of claim 20, wherein the elastic waistband is partially elongated when attached to the chassis.

22. The absorbent garment of claim 13, comprising a diaper.

23. The absorbent garment of claim 13, comprising swim wear.

24. The absorbent garment of claim 13, comprising child training pants.

25. The absorbent garment of claim 13, comprising an adult incontinence garment.

26. A method of preparing a laminate with independently movable layers, comprising the steps of:
extruding a film layer, the film layer having a length and a width;
providing an elastic nonwoven layer having a length and a width substantially equal to the length and the width of the film layer;
aligning the elastic nonwoven layer with the film layer; and
partially bonding the elastic nonwoven layer to the film layer such that at least 70% of a bonded area is located in a peripheral region of each of the layers, leaving a central region of each layer unbonded.

27. The method of claim 26, wherein at least 80% of the bonded area is located in the peripheral region of at least one of the layers.

28. The method of claim 26, wherein at least 90% of the bonded area is located in the peripheral region of at least one of the layers.

29. The method of claim 26, wherein roughly 100% of the bonded area is located in the peripheral region of at least one of the layers.

30. The method of claim 26, wherein between about 5% and about 60% of a surface of the elastic nonwoven layer is bonded to a surface of the film layer.

31. The method of claim 26, wherein between about 7% and about 50% of a surface of the elastic nonwoven layer is bonded to a surface of the film layer.

32. The method of claim 26, wherein between about 10% and about 25% of a surface of the elastic nonwoven layer is bonded to a surface of the film layer.

* * * * *

UNITED STATES PATENT AND TRADEMARK OFFICE
CERTIFICATE OF CORRECTION

PATENT NO. : 6,679,869 B1
DATED : January 20, 2004
INVENTOR(S) : Daniel Robert Schlinz et al.

It is certified that error appears in the above-identified patent and that said Letters Patent is hereby corrected as shown below:

Column 15,
Line 4, replace the existing equation with the following equation:

-- $WVTR = F\rho_{sat}(T)RH/A\rho_{sat}(T)(1-RH)$ --

Line 8, replace "$p_{sat}(T)$" with -- $\rho_{sat}(T)$ --

Signed and Sealed this

Twenty-eighth Day of September, 2004

JON W. DUDAS
*Director of the United States Patent and Trademark Office*